US008926589B2

United States Patent
Govari

(10) Patent No.: US 8,926,589 B2
(45) Date of Patent: *Jan. 6, 2015

(54) PRE-FORMED CURVED ABLATION CATHETER

(71) Applicant: Biosense Webster (Israel), Ltd., Yokneam (IL)

(72) Inventor: Assaf Govari, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/765,044

(22) Filed: Feb. 12, 2013

(65) Prior Publication Data

US 2013/0158539 A1  Jun. 20, 2013

Related U.S. Application Data

(62) Division of application No. 12/636,064, filed on Dec. 11, 2009.

(51) Int. Cl.
   *A61M 25/01* (2006.01)
   *A61B 18/18* (2006.01)
   *A61B 18/14* (2006.01)
   *A61B 17/00* (2006.01)
   *A61B 19/00* (2006.01)

(52) U.S. Cl.
   CPC .............. *A61B 18/18* (2013.01); *A61B 18/1492* (2013.01); *A61B 2017/00867* (2013.01); *A61B 2019/467* (2013.01); *A61B 2019/5251* (2013.01); *C08L 2201/12* (2013.01)
   USPC ............................................. 604/530; 606/41

(58) Field of Classification Search
   USPC ................................. 606/41, 49; 604/530, 20
   See application file for complete search history.

(56) References Cited

U.S. PATENT DOCUMENTS

| | | | | |
|---|---|---|---|---|
| 4,671,795 A | * | 6/1987 | Mulchin | 604/530 |
| 5,109,830 A | * | 5/1992 | Cho | 600/108 |
| 5,487,385 A | | 1/1996 | Avitall | |
| 5,626,136 A | * | 5/1997 | Webster, Jr. | 600/373 |
| 5,823,955 A | | 10/1998 | Kuck et al. | |
| 5,882,346 A | * | 3/1999 | Pomeranz et al. | 604/525 |
| 5,885,259 A | | 3/1999 | Berg | |
| 5,916,214 A | | 6/1999 | Cosio et al. | |
| 6,064,902 A | | 5/2000 | Haissaguerre et al. | |
| 6,146,381 A | * | 11/2000 | Bowe et al. | 606/41 |

(Continued)

FOREIGN PATENT DOCUMENTS

EP  2047797 A  4/2009
WO  WO 02/38064 A  5/2002

OTHER PUBLICATIONS

Japanese Notification of Reasons for Refusal dated Jul. 15, 2014 in corresponding Japanese Patent Application No. 2010-275491.

*Primary Examiner* — Joseph Stoklosa
*Assistant Examiner* — Jocelyn D Ram

(57) ABSTRACT

A medical device includes an insertion tube, having a longitudinal axis and having a distal end adapted for insertion through a body passage into a cavity within a body of a patient. An electrode is located on the distal end of the insertion tube and is configured to contact tissue in the cavity. A resilient member is contained within the distal end of the insertion tube and is configured, when unconstrained, to cause the distal end to bend away from the longitudinal axis in a curved shape and to straighten toward the longitudinal axis when subjected to a force.

7 Claims, 3 Drawing Sheets

(56) References Cited

U.S. PATENT DOCUMENTS

| | | | |
|---|---|---|---|
| 6,272,371 B1* | 8/2001 | Shlomo | 600/424 |
| 6,542,781 B1 | 4/2003 | Koblish et al. | |
| 6,652,517 B1* | 11/2003 | Hall et al. | 606/41 |
| 6,973,339 B2* | 12/2005 | Govari | 600/374 |
| 7,122,034 B2* | 10/2006 | Belhe et al. | 606/41 |
| 8,608,735 B2* | 12/2013 | Govari et al. | 606/41 |
| 2002/0183638 A1 | 12/2002 | Swanson | |
| 2005/0267460 A1 | 12/2005 | Roop et al. | |
| 2006/0241366 A1* | 10/2006 | Falwell et al. | 600/374 |
| 2006/0253116 A1* | 11/2006 | Avitall et al. | 606/41 |
| 2007/0062546 A1* | 3/2007 | Viswanathan et al. | 128/898 |
| 2007/0066878 A1* | 3/2007 | Worley et al. | 600/374 |
| 2007/0161882 A1* | 7/2007 | Pappone | 600/374 |
| 2007/0179492 A1* | 8/2007 | Pappone | 606/32 |
| 2009/0306650 A1 | 12/2009 | Govari et al. | |
| 2010/0168549 A1 | 7/2010 | Pappone | |
| 2011/0152856 A1* | 6/2011 | Govari et al. | 606/34 |
| 2011/0160719 A1* | 6/2011 | Govari et al. | 606/41 |
| 2012/0165667 A1* | 6/2012 | Altmann et al. | 600/439 |
| 2013/0096551 A1 | 4/2013 | Govari et al. | |
| 2013/0131489 A1 | 5/2013 | Govari et al. | |
| 2013/0131663 A1 | 5/2013 | Govari et al. | |

* cited by examiner

PRE-FORMED CURVED ABLATION CATHETER

This application is a divisional of U.S. application Ser. No. 12/636,064 filed Dec. 11, 2009, the complete disclosure of which is hereby incorporated herein by reference for all purposes.

FIELD OF THE INVENTION

The present invention relates generally to methods and devices for invasive medical treatment, and specifically to catheters.

BACKGROUND OF THE INVENTION

Ablation of myocardial tissue is well known as a treatment for cardiac arrhythmias. In radio-frequency (RF) ablation, for example, a catheter is inserted into the heart and brought into contact with tissue at a target location. RF energy is then applied through an electrode on the catheter in order to create a lesion for the purpose of breaking arrhythmogenic current paths in the tissue.

Recently, circumferential ablation of the ostia of the pulmonary veins has gained acceptance as a treatment for atrial arrhythmias, and particularly for atrial fibrillation. For example, U.S. Pat. No. 6,064,902, whose disclosure is incorporated herein by reference, describes a catheter for ablating tissue on the inner wall of a blood vessel, such as a pulmonary vein. The tip portion of the catheter is deflectable from a first, generally straight, configuration, in which the proximal and distal sections are substantially co-linear, to a second, J-shaped, configuration in which the proximal and distal sections are generally parallel with a separation therebetween substantially corresponding to the inside diameter of the blood vessel. The distal end portion of the catheter is rotated about the longitudinal axis of the catheter to cause a circumferential displacement of proximal and distal ablation electrodes on the catheter along the inner wall of the pulmonary vein. In this way, the electrode catheter may be used to ablate a number of circumferentially-spaced sites on the inner wall of the pulmonary vein by ablating one or two sites at each circumferential position.

SUMMARY OF THE INVENTION

Embodiments of the present invention that are described hereinbelow provide invasive devices and methods for contacting tissue within the body with enhanced safety and efficacy.

There is therefore provided, in accordance with an embodiment of the present invention, a medical device, including an insertion tube, having a longitudinal axis and having a distal end adapted for insertion through a body passage into a cavity within a body of a patient. An electrode is located on the distal end of the insertion tube and is configured to contact tissue in the cavity. A resilient member, which may include a shape memory material, is contained within the distal end of the insertion tube and is configured, when unconstrained, to cause the distal end to bend away from the longitudinal axis in a curved shape and to straighten toward the longitudinal axis when subjected to a force.

In a disclosed embodiment, the device includes at least one position transducer in the distal end of the insertion tube. The at least one position transducer may be configured to measure a bend angle of the distal end of the insertion tube. In this case, the at least one position transducer typically includes two position transducers at different longitudinal locations within the distal end of the insertion tube.

Typically, the resilient member is configured to straighten toward the longitudinal axis when the force is applied in an inward radial force. The resilient member may be configured to buckle when the radial force exceeds a predetermined threshold.

There is also provided, in accordance with an embodiment of the present invention, medical apparatus, including a sheath, which has a longitudinal axis and a distal opening and is adapted for insertion through a body passage into a cavity within a body of a patient. A catheter is configured for insertion through the sheath into the cavity and has a resilient distal end that is formed so that, when unconstrained, the distal end bends away from the longitudinal axis in a curved shape, and when subjected to a force, the distal end straightens toward the longitudinal axis.

In a disclosed embodiment, the sheath exerts the force in an inward radial direction so as to straighten the distal end of the catheter during passage of the distal end through the sheath, and the distal end of the catheter assumes the curved shape after passing through the distal opening of the sheath into the cavity. Typically, the catheter is configured to rotate about the axis within the sheath.

In some embodiments, the catheter includes an electrode at the distal end, which is configured to contact tissue in the cavity. The apparatus may include a radio frequency (RF) generator, which is coupled to supply RF energy through the catheter to the electrode so as to ablate the tissue.

In a disclosed embodiment, the catheter includes a position transducer in the distal end, and the apparatus includes a position sensing system, which is configured to communicate with the position transducer so as to determine a location of the distal end within the body. The position sensing system may be configured to provide an indication of a bend angle of the distal end of the catheter.

There is additionally provided, in accordance with an embodiment of the present invention, a method for medical treatment, including inserting a sheath, having a longitudinal axis and a distal opening, through a body passage into a cavity within a body of a patient. A catheter is inserted into the sheath, wherein the catheter has a resilient distal end that is formed so that, when unconstrained, the distal end bends away from the longitudinal axis in a curved shape, and when subjected to a force, the distal end straightens toward the longitudinal axis. The catheter is advanced through the sheath so that the distal end of the catheter passes through the distal opening of the sheath into the cavity and assumes the curved shape. The catheter is manipulated within the cavity so that the distal end contacts tissue in the cavity, and the catheter is moved within the sheath while the distal end contacts the tissue so as to cause the distal end to trace a desired path along the tissue.

In some embodiments, moving the catheter includes rotating the catheter about the axis. In one embodiment, the cavity includes a blood vessel, and rotating the catheter causes the distal end to trace a circular path around an internal circumference of the blood vessel. For example, inserting the sheath may include passing the sheath percutaneously through a vascular system of the patient into a left atrium of a heart of the patient, and advancing the catheter may include positioning the distal end of the catheter in a pulmonary vein so as to trace the circular path within an ostium of the pulmonary vein.

In a disclosed embodiment, the method includes providing an indication of a bending angle of the distal end of the catheter, and controlling a pressure of the distal end against the tissue responsively to the indication.

The present invention will be more fully understood from the following detailed description of the embodiments thereof, taken together with the drawings in which:

DETAILED DESCRIPTION OF EMBODIMENTS

Figure 1:
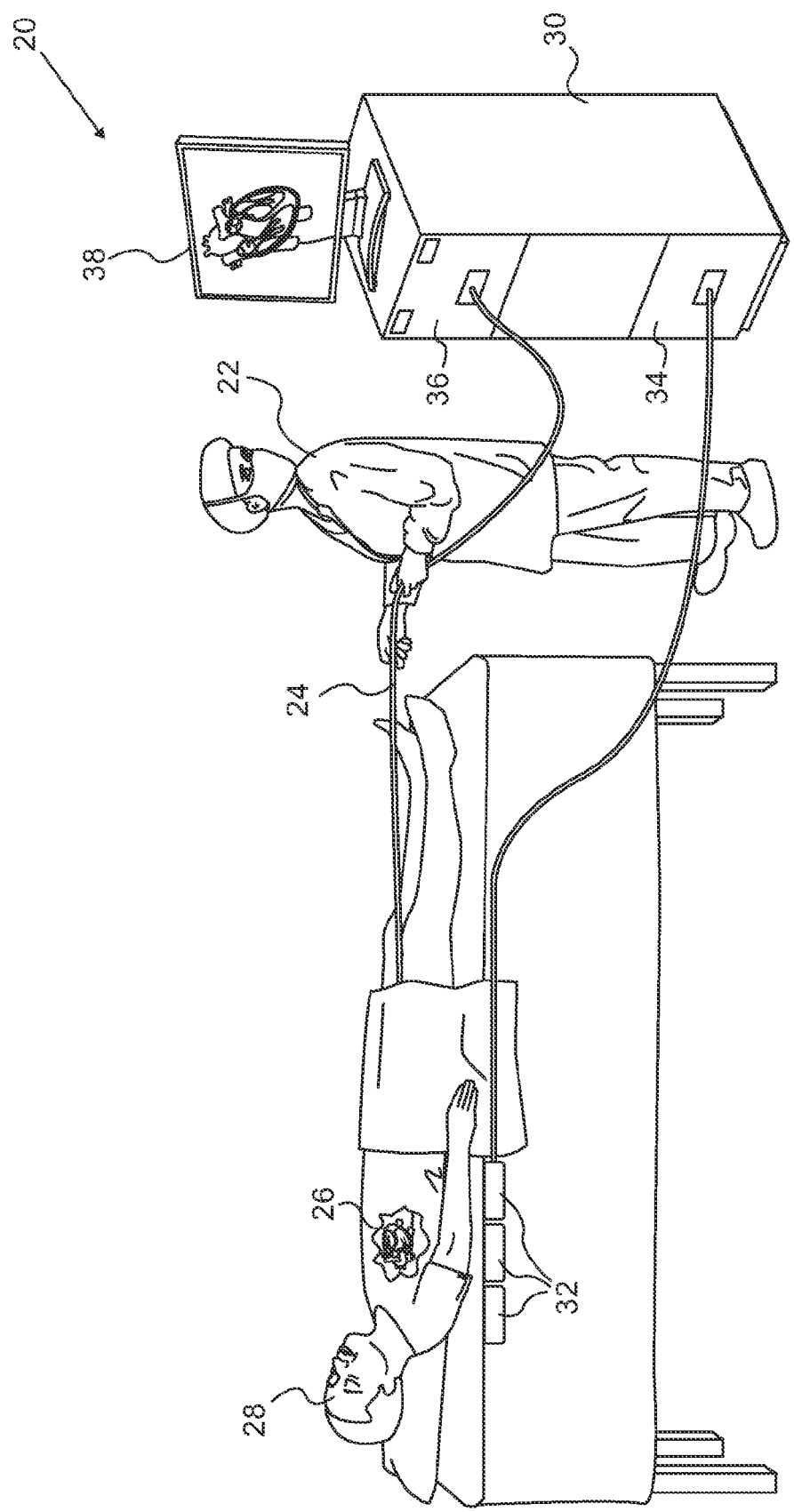
FIG. 1 is a schematic pictorial illustration of a system for ablation of tissue in the heart, in accordance with an embodiment of the present invention.

Embodiments of the present invention that are described hereinbelow provide simple, safe, and reliable devices and methods for ablating tissue along a selected path inside a body cavity. Some of these embodiments are particularly suitable for ablating circumferential paths inside a tubular structure, such as a blood vessel. The principles of the present invention may also be applied, however, on linear paths and in applications other than ablation.

In a disclosed embodiment, a medical device, such as a catheter, comprises an insertion tube, which is inserted through a body passage into a body cavity, such as a chamber of the heart. The insertion tube has an electrode at its distal tip, which makes contact with tissue in the cavity. The distal end of the insertion tube contains a resilient member, such as a shape memory strut, which is pre-formed so as to cause the distal end to bend away from the longitudinal axis of the insertion tube in a curved shape as long as the catheter is not constrained by a radial force. In other words, the unconstrained shape of the distal end of the catheter is bent, and the catheter assumes this shape without the use of any sort of active steering mechanism.

When a force is applied against the distal tip of the catheter in the appropriate direction, such as an inward radial force, it causes the distal end to straighten toward the longitudinal axis. The bend angle thus gives an indication of the force with which the catheter tip is pressing against the tissue. The distal tip of the catheter may be made structurally weak enough to buckle if the pressure against the tissue is greater than a certain threshold, thus giving an extra measure of safety against excessive pressure that might otherwise puncture the tissue This pre-formed curved catheter may be used to ablate tissue along circumferential paths inside the pulmonary veins. For this purpose, a sheath is inserted into the left atrium, typically via the fossa ovalis, and is positioned coaxially with the pulmonary vein in which the ablation is to be performed. The catheter is passed through the sheath (which radially constrains the catheter to remain straight while passing through the sheath) until the distal end of the catheter projects out of the sheath and into the vein. The curved shape of the distal end projecting out of the sheath causes the electrode at the distal tip of the catheter to contact the inner wall of the vein. The angle and length of the curved end of the catheter are chosen so that the distal tip presses against the inner wall of the vein when the longitudinal axis of the sheath and the catheter insertion tube is aligned with the axis of the vein.

To carry out the ablation, an operator manipulates the catheter so that the electrode contacts the tissue in the ostium of the vein, and then rotates the shaft of the catheter in the sheath while applying RF energy to the electrode. This rotation causes the electrode to move around the inner circumference of the vein in a circular path and to ablate the tissue along the path as it goes. Alternatively, the RF energy may be actuated intermittently to ablate selected points along the path. Further alternatively or in addition to this rotational movement, the physician may apply other movements in order to trace different sorts of paths with the catheter.

FIG. 1 is a schematic pictorial illustration of a system 20 for ablation of tissue in a heart 26 of a patient 28, in accordance with an embodiment of the present invention. An operator 22, such as a cardiologist, inserts a catheter 24 through the vascular system of patient 28 so that the distal end of the catheter enters a chamber of the patient's heart. Operator 22 advances the catheter so that its distal tip engages endocardial tissue at a desired location or locations, as shown in the figures that follow. Catheter 24 is connected by a suitable connector at its proximal end to a console 30. The console comprises a RF generator 36 for applying RF energy through an electrode at the distal tip of the catheter in order to ablate the tissue contacted by the distal tip. Alternatively or additionally, catheter 24 may be used for other diagnostic and/or therapeutic functions, such as intracardiac electrical mapping or other types of ablation therapy.

Figure 3:
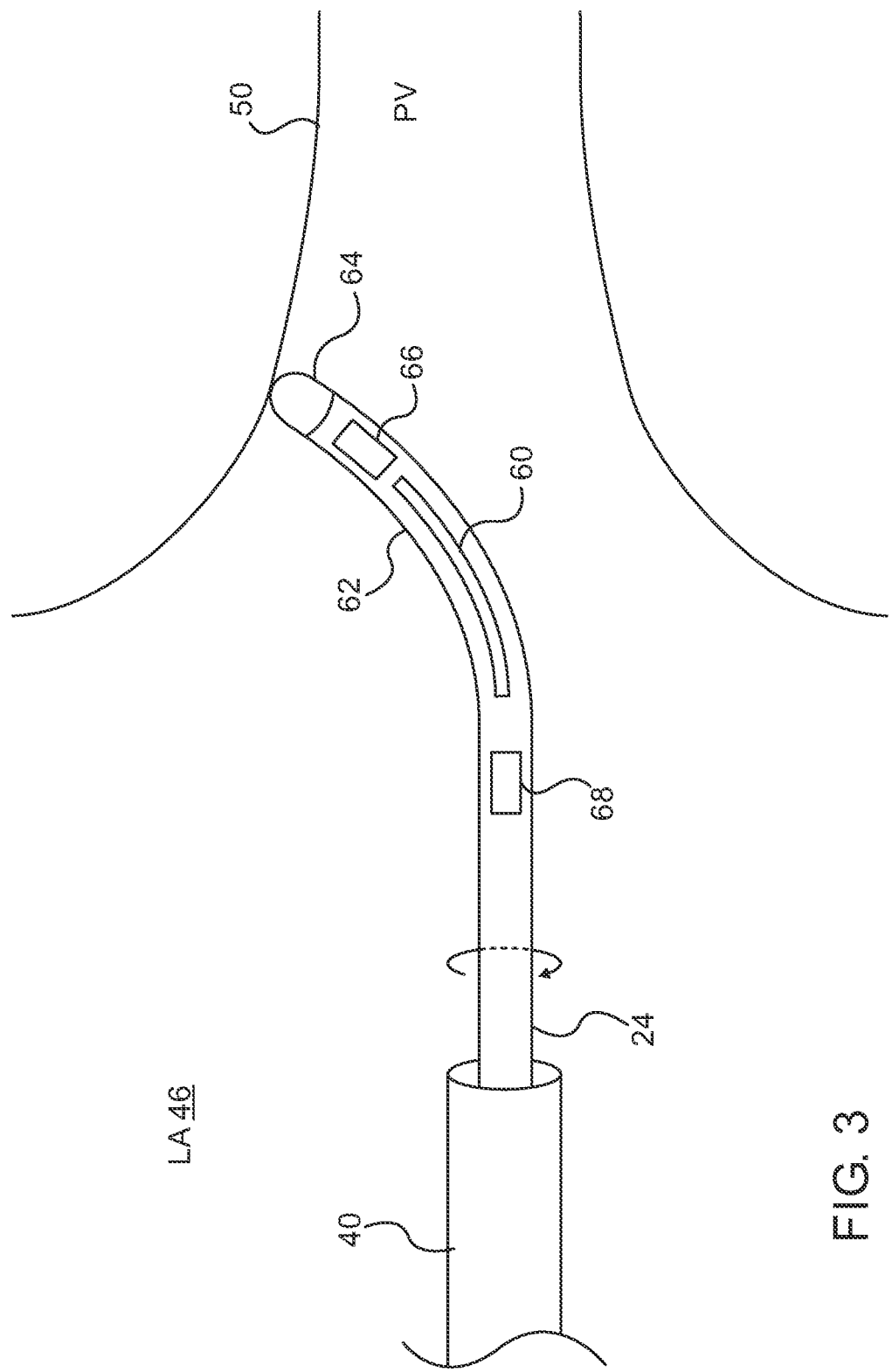
FIG. 3 is a schematic side view of a catheter within the ostium of a pulmonary vein, in accordance with an embodiment of the present invention.

In the pictured embodiment, system 20 uses magnetic position sensing to determine position coordinates of the distal end of the catheter inside heart 26. To determine the position coordinates, a driver circuit 34 in console 30 drives field generators 32 to generate magnetic fields within the body of patient 28. Typically, field generators 32 comprise coils, which are placed below the patient's torso at known positions external to the body. These coils generate magnetic fields in a predefined working volume that contains heart 26. One or more magnetic field sensors within the distal end of catheter (as shown in FIG. 3) generate electrical signals in response to these magnetic fields. The console processes these signals in order to determine the position (location and/or orientation) coordinates of the distal end of catheter 24, and possibly also the bend angle, as explained below. Console 30 may use the coordinates in driving a display 38 to show the location and status of the catheter. This method of position sensing and processing is implemented, for example, in the CARTO™ system produced by Biosense Webster Inc. (Diamond Bar, Calif.).

Alternatively or additionally, system 20 may comprise an automated mechanism (not shown) for maneuvering and operating catheter 24 within the body of patient 28. Such mechanisms are typically capable of controlling both the longitudinal motion (advance/retract) and the rotation of catheter 24. In such embodiments, console 30 generates a control input for controlling the motion of the catheter based on the signals provided by the position sensing system.

Although FIG. 1 shows a particular system configuration, other system configurations may be used in alternative embodiments of the present invention. For example, the methods described hereinbelow may be applied using position transducers of other types, such as impedance-based or ultrasonic position sensors. The term "position transducer" as used herein refers to an element mounted on or in catheter 24 that causes console 30 to receive signals indicative of the coordinates of the element. The position transducer may thus comprise a receiver in the catheter, which generates a position signal to the control unit based on energy received by the transducer; or it may comprise a transmitter, emitting energy that is sensed by a receiver external to the probe. Furthermore, the methods described hereinbelow may similarly be applied in mapping and measurement applications using not only catheters, but also probes of other types, both in the heart and in other body organs and regions.

Figure 2:
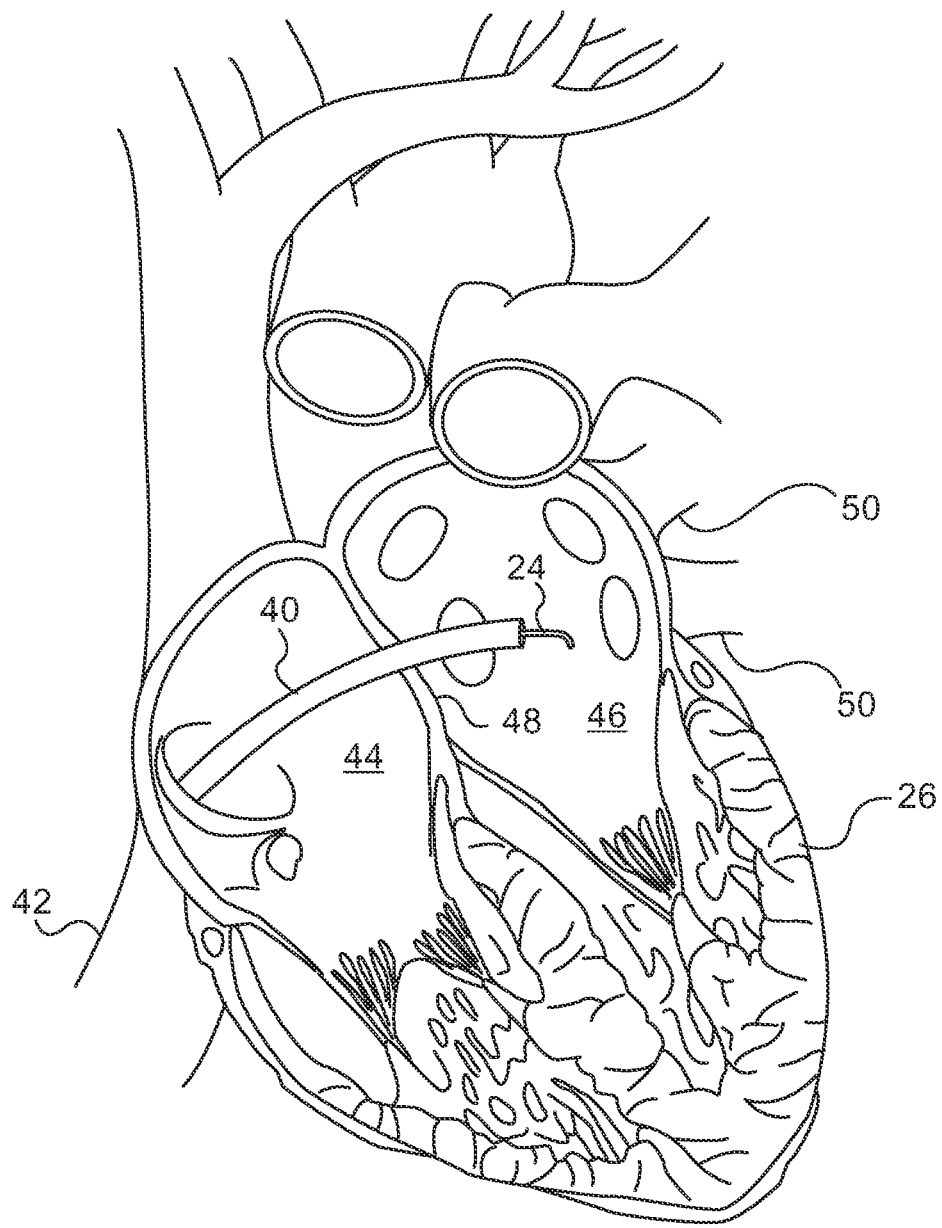
FIG. 2 is a schematic sectional view of a heart showing insertion of a catheter into the left atrium, in accordance with an embodiment of the present invention.

FIG. 2 is a schematic sectional view of heart 26 showing insertion of catheter 24 into the heart, in accordance with an embodiment of the present invention. To insert the catheter in the pictured embodiment, the operator first passes a sheath 40 percutaneously through the vascular system and into right atrium 44 of the heart through ascending vena cava 42. The sheath penetrates through interatrial septum 48, typically via the fossa ovalis, into left atrium 46. Alternatively, other approach paths may be used. Catheter 24 is then inserted through the sheath until the distal end of the catheter passes out of the distal opening at the end of the sheath into the left atrium, as shown in the figure.

Operator 22 aligns the longitudinal axis of sheath 40 and catheter 24 inside left atrium 46 with the axis of one of pulmonary veins 50. The operator may carry out this alignment using the position sensing methods described above, along with a pre-acquired map or image of heart 26. Alternatively or additionally, the alignment may be performed under fluoroscopic or other means of visualization. The operator inserts the distal tip of the catheter into the target pulmonary vein and brings the catheter tip into contact with the ostium. The operator then rotates the catheter about its axis within the sheath in order to trace a circular path around the internal circumference of the vein. Meanwhile, the operator actuates RF generator 36 to ablate the tissue along the path. After completing this procedure in one pulmonary vein, the operator may shift the sheath and catheter and repeat the procedure in one or more of the other pulmonary veins.

Alternatively or additionally, operator 22 may advance and/or retract catheter 24 through sheath 40 in order to trace (and possibly ablate) linear paths along the heart wall, either in left atrium 46 or elsewhere.

The above procedures may be carried out without the use of any steering mechanism in catheter 24: Due to the curved shape of the catheter, only advancement/retraction and rotation of the catheter are required. The absence of an internal steering mechanism reduces the size and cost of the catheter relative to devices that are known in the art. As noted earlier, the above procedures may be carried out by an automated mechanism, rather than manually by the operator as illustrated in FIG. 1.

FIG. 3 is a schematic side view showing details of the distal end of catheter 24 within the ostium of pulmonary vein 50, in accordance with an embodiment of the present invention. Catheter 24 comprises an insertion tube 62, which is typically made from a biocompatible plastic, such as polyurethane, and contains the functional elements of the catheter. The longitudinal axis of the insertion tube (except for the bent distal end) is aligned with the longitudinal axis of sheath 40.

A resilient member 60 inside the distal end of insertion tube 62 is pre-formed in a bent shape. Member 60 may comprise, for example, a strut, rod or tube made from a shape memory material, such as Nitinol, which is produced so as to have this bent shape when unconstrained in its austenitic state. When an inward radial force is exerted against the bent distal end, it straightens toward the longitudinal axis. Thus, within sheath 40 catheter 24 is held straight by the sheath itself. Pressure of the catheter tip against the ostium of vein (or against other tissue) will also tend to straighten the distal end of the catheter. Resilient member 60 may be made structurally weak enough to buckle if the pressure against the catheter tip is greater than a certain predetermined threshold, thus giving an extra measure of safety against excessive pressure that could otherwise puncture the vein or heart wall.

Catheter 24 comprises an electrode 64 at the distal tip of insertion tube 62. This electrode is connected by a conductor (not shown) running through the catheter to RF generator 36, which thus provides RF energy to ablate the tissue with which the electrode is in contact. Rotating catheter 24 about its axis, as illustrated by the circular arrow in FIG. 3, causes electrode 64 to trace a circular path around the inner circumference of the ostium of vein 50. Operator 22 is thus able to create a circular ablation lesion easily and reliably.

Catheter 24 comprises position sensors 66 and 68 at different longitudinal locations within the distal end of insertion tube 62. In the embodiment shown in FIG. 1 and described above, sensors 66 and 68 comprise coils, which sense the magnetic fields produced by field generators 32 and output signals to console 30. The console process these signals in order to find the location and orientation coordinates of the coils. The difference between the orientations of sensors 66 and 68 indicates the bend angle (or equivalently, the curvature) of the distal end of the catheter. Alternatively, the bend angle may be measured using position transducers or bend sensors of other types. Additionally or alternatively, operator 22 may observe the bend angle fluoroscopically.

Reduction of the bend angle (straightening of the distal end) relative to the bend angle of the distal end when unconstrained is indicative of the radial force exerted on the distal tip of catheter 24 by the tissue with which it is in contact: The harder the operator presses the tip radially against the tissue, the smaller will be the bend angle. Console 30 may present an indication of the bend angle, such as a graphical representation of the distal end of the catheter, on display 38. Operator 22 can then control the radial pressure exerted by the catheter against the tissue in heart 26 so that the bend angle remains within a suitable range. Typically, a small degree of unbending of the distal end of the catheter is desirable to ensure that electrode 64 contacts the tissue firmly; but too much unbending is to be avoided in order to prevent puncturing of the tissue due to excessive pressure. Alternatively or additionally, the bend angle of the catheter may be monitored and controlled automatically.

Although the above embodiments relate specifically to treatment in and around the pulmonary veins, the design features of catheter 24 and of system 20 generally may also be used for treatment inside other veins and arteries, as well as in other sorts of body cavities, both tubular and of other shapes. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

What is claimed is:

1. A method for medical treatment, comprising:
   inserting a sheath, having a longitudinal axis and a distal opening, through a body passage into a cavity within a body of a patient;
   inserting into the sheath a catheter having a resilient distal end that is formed so that, when unconstrained, the distal end bends away from the longitudinal axis in a curved shape consisting of a single arcuate segment, and when subjected to a force, the distal end straightens toward the longitudinal axis, the catheter further comprising a first and second magnetic position transducers, wherein the first magnetic position transducer is positioned proximal the resilient distal end and the second magnetic position transducer is positioned near the distal end of the resilient distal end;

advancing the catheter through the sheath so that the distal end of the catheter passes through the distal opening of the sheath into the cavity and assumes the curved shape;

manipulating the catheter within the cavity so that the distal end contacts tissue in the cavity;

generating magnetic fields with magnetic field generators;

sensing the magnetic fields produced by the field generators with the magnetic position transducers and outputting signals to a processor;

processing the signals in the processor to determine the bend angle of the of the distal end of the catheter and the radial force exerted thereon by tissue within the body cavity; and moving the catheter within the sheath while the distal end contacts the tissue so as to cause the distal end to trace a desired path along the tissue.

2. The method according to claim 1, wherein moving the catheter comprises rotating the catheter about the axis.

3. The method according to claim 1, wherein the cavity comprises a blood vessel, and wherein rotating the catheter causes the distal end to trace a circular path around an internal circumference of the blood vessel.

4. The method according to claim 3, wherein inserting the sheath comprises passing the sheath percutaneously through a vascular system of the patient into a left atrium of a heart of the patient, and wherein advancing the catheter comprises positioning the distal end of the catheter in a pulmonary vein so as to trace the circular path within an ostium of the pulmonary vein.

5. The method according to claim 1, and comprising applying energy through the catheter so as to ablate the tissue along the path.

6. The method according to claim 5, wherein the catheter comprises an electrode at the distal end, and wherein applying the energy comprises supplying radio-frequency (RF) electrical energy to the electrode.

7. The method according to claim 1, and comprising providing an indication of a bending angle of the distal end of the catheter, and controlling a pressure of the distal end against the tissue responsively to the indication.

* * * * *